(12) United States Patent
Guenther et al.

(10) Patent No.: US 9,447,295 B2
(45) Date of Patent: Sep. 20, 2016

(54) INK-JET PRINTING INK COMPRISING N-VINYLOXAZOLIDINONE

(71) Applicant: BASF SE, Ludwigshafen (DE)

(72) Inventors: Erhard Guenther, Hassloch (DE); Radwan Abdallah, Ludwigshafen (DE); Giovanni Dandola, Heidelberg (DE); Dagmar Pascale Kunsmann-Keitel, Limburgerhof (DE); Edouard Loisel, Leimen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/910,965

(22) PCT Filed: Aug. 5, 2014

(86) PCT No.: PCT/EP2014/066767
§ 371 (c)(1),
(2) Date: Feb. 8, 2016

(87) PCT Pub. No.: WO2015/022228
PCT Pub. Date: Feb. 19, 2015

(65) Prior Publication Data
US 2016/0193852 A1    Jul. 7, 2016

(30) Foreign Application Priority Data
Aug. 12, 2013 (EP) .................... 13180035.1

(51) Int. Cl.
*B41J 11/00* (2006.01)
*C09D 11/101* (2014.01)
*C09D 11/106* (2014.01)
*C09D 11/30* (2014.01)

(52) U.S. Cl.
CPC ............ *C09D 11/101* (2013.01); *B41J 11/002* (2013.01); *C09D 11/106* (2013.01); *C09D 11/30* (2013.01)

(58) Field of Classification Search
None
See application file for complete search history.

(56) References Cited

U.S. PATENT DOCUMENTS

| 4,113,895 A * | 9/1978 | Watt ................... B41M 7/0045 427/410 |
| 4,639,472 A | 1/1987 | Green et al. |
| 4,774,309 A | 9/1988 | Green et al. |
| 4,831,153 A | 5/1989 | Phung |
| 2012/0015159 A1 | 1/2012 | Herlihy et al. |

FOREIGN PATENT DOCUMENTS

| EP | 0 279 303 A2 | 8/1988 |
| EP | 0 555 069 A1 | 8/1993 |
| JP | 57-109813 A | 7/1982 |
| WO | WO 2010/057839 A1 | 5/2010 |
| WO | WO 2010/103281 A1 | 9/2010 |

OTHER PUBLICATIONS

International Search Report and Written Opinion issued Oct. 24, 2014 in PCT/EP2014/066767.

* cited by examiner

*Primary Examiner* — Lisa M Solomon
(74) *Attorney, Agent, or Firm* — Oblon, McClelland, Maier & Neustadt, L.L.P.

(57) ABSTRACT

Use of a radiation curable composition as printing ink for ink-jet printing, wherein the radiation curable composition comprises N-vinyloxazolidinone of formula (I) in which $R_1$ to $R_4$ independently from each other are a hydrogen atom or an organic radical having not more than 10 carbon atoms.

12 Claims, No Drawings

INK-JET PRINTING INK COMPRISING N-VINYLOXAZOLIDINONE

The invention relates to the use of a radiation curable composition as printing ink for ink-jet printing, wherein the radiation curable composition comprises N-vinyloxazolidinone of formula I

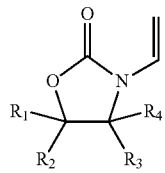

in which $R_1$ to $R_4$ independently from each other are a hydrogen atom or an organic radical having not more than 10 carbon atoms.

Often radiation curable compositions are used as printing inks. With radiation curable compositions no solvents which have to be removed during or after the printing process are required. Even without solvent, the printing ink should be fluid at room temperature. For this purpose, printing inks frequently comprise so-called reactive diluents; these are low molecular weight compounds which become part of the resulting coating after curing. The choice of reactive diluents also affects the performance characteristics of the imprinted substrates obtained.

EP-A-555 069 discloses that the performance characteristics of radiation curable compositions can be improved by adding solid monomers, in particular N-vinylcaprolactam. However, the handling of such solid monomers is disadvantageous. According to WO 2010/057839 N-vinylcaprolactam may be replaced by a mixture of N-vinylcaprolactam with an N-vinylamide.

U.S. Pat. No. 4,639,472 discloses radiation curable compositions comprising N-vinyloxazolidinone. Printing inks are mentioned as one possible application of such radiation curable compositions.

A printing process of particular importance is ink-jet printing. In an ink-jet printing process droplets of the printing ink are electrically charged to a specific degree. The droplets bearing such specific electrical charge are subjected to an electrostatic field which deflects the droplets on their way to the substrate to be printed. Droplets bearing a higher charge are more deflected by the electrostatic field, thus obtaining the desired print. It is known to use radiation curable compositions as printing ink for ink-jet printing.

In the case of ink-jet printing inks, in particular of UV-curable ink-jet printing inks, it is important that the adhesion of the printing ink to the substrate to be printed is very good. Particularly critical is the adhesion to nonpolar, plastic substrates like polypropylene. Furthermore in ink-jet printing processes a low viscosity of the printing ink is important, which allows the quick and easy formation of droplets. UV-curable inks for ink-jet printing usually are free of solvents, hence the radiation curable compounds themselves should have a sufficient low viscosity. In addition, a high reactivity in radiation curing is required, so that the printing and curing process runs quick and easily.

Object of the present invention were printing inks, in particular radiation curable printing inks, for ink-jet printing. The printing inks should have a high reactivity in radiation curing, a low viscosity and should allow an ink-jet printing process with good characteristics regarding the performance of the process and the printed substrate obtained. In particular the printing ink should have a good adhesion to nonpolar substrates, for example to polypropylene.

Accordingly, an ink-jet printing process wherein the above radiation curable composition is used as printing ink has been found.

The radiation curable composition which is used as printing ink in ink-jet printing comprises an N-vinyloxazolidinone of formula I

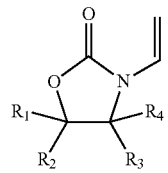

in which $R_1$ to $R_4$ independently from each other are a hydrogen atom or an organic radical having not more than 10 carbon atoms.

Preferably at least two of $R_1$ to $R_4$ in formula I are a hydrogen atom.

In a particular preferred embodiment and least two of $R_1$ to $R_4$ in formula I are a hydrogen atom and any remaining $R_1$ to $R_4$ are an organic radical having not more than 10 carbon atoms.

Preferably the organic radical has not more than 4 carbon atoms.

In a particular preferred embodiment the organic radical is an alkyl or alkoxy radical.

In a preferred embodiment the organic radical is a C1 to C4 alkyl radical or a C1 to C4 alkoxy radical.

In a most preferred embodiment the organic radical is a methyl radical.

As examples of N-vinyloxazolidinone of formula I compounds may be mentioned, wherein all of $R_1$ to $R_4$ are a hydrogen atom (for short NVO) or $R_1$ is a C1 to C4 alkyl radical, in particular a methyl radical, and all of $R_2$ to $R_4$ are a hydrogen atom (N-vinyl-5-methyl oxazolidinone, for short NVMO) or $R_1$ and $R_2$ are a hydrogen atom and $R_3$ and $R_4$ are a C1 to C4 alkyl radical, in particular a methyl radical.

Particularly preferred are NVO and NVMO, most preferred is NVMO.

It is understood that any reference to the N-vinyloxazolidinone in this patent specification includes also a mixture of different N-vinyloxazolidinones of formula I.

The synthesis of N-vinyloxazolidinone compounds of formula I is known. N-vinyloxazolidinone may be produced according to the process described in U.S. Pat. No. 4,831,153 by pyrolyzing N-(1-hydroxyalkyl)-2-oxazolidinone. Preferably it is synthesized according to the well-known Reppe process by reacting acetylene with oxazolidinone.

After synthesis the N-vinyloxazolidinon may be stabilized in order to prevent premature polymerization.

Suitable stabilizers are all customary stabilizers which prevent premature polymerization in the case of N-vinyloxazolidinon of the formula I. Mixtures of stabilizers are also particularly suitable. Nitroxyl compounds, such as 1-oxyl-2,2,6,6-tetramethylpiperidine, 4-hydroxy-1-oxyl-2,2,6,6-tetramethylpiperidine, phenol derivatives having at least one substituent in the alpha-position to the phenol group, such as 2,6-di-tert-butyl-4-methylphenol, tocopherols, quinones and hydroquinones, such as hydroquinone monomethyl ether, N-oxyl compounds, aromatic amines and phenylenediamines, imines, sulfonamides, oximes, hydroxylamines, urea derivatives, phosphorus-containing compounds, sulfur-containing compounds, complexing agents based on tetraazaannulene (TAA) and/or metal salts, and, if appropriate, mixtures thereof, may be mentioned as stabilizers. Phosphorus-containing compounds are, for example, triphenylphosphine, triphenylphosphite, hypophosphorous acid, trinonyl phosphite, triethyl phosphite or diphenylisopropylphosphine.)

The radiation curable composition preferably comprises at least 0.5% by weight, particularly preferably at least 2.5% by weight, more preferably at least 5% by weight and in a particularly preferred embodiment at least 10% by weight of the N-vinyloxazolidinone.

The radiation curable composition preferably comprises up to 80% by weight, particularly preferably up to 60% by weight, more preferably up to 50% by weight and in a particularly preferred embodiment up to 40% by weight, respectively up to 30% by weight of the N-vinyloxazolidinone.

Hence the radiation curable composition which is used as ink-jet printing ink may comprise for example from 0.5 to 50% by weight, particularly from 2.5 to 40% by weight and particularly preferred from 5 to 30% by weight of the N-vinyloxazolidinone.

All above percentages by weight are based on the total radiation curable composition which is used as ink-jet printing ink.

The radiation curable composition may comprise further constituents, for example further radiation curable compounds or additives, such as stabilizers, photoinitiators etc.

Further radiation curable compounds may be compounds with polymerizable, ethylenically unsaturated groups as, for example, vinyl groups, as vinyl ether, vinyl ester or N-vinyl groups, allyl groups or (meth)acryloyl groups.

The expression "(meth)acrylol group" stands for a acrylol group or a methacryloyl group, preferably an acryloly group.

Compounds with at least one (meth)acryloyl group are hereinafter referred to as (meth)acryloyl compounds for short.

Such further radiation curable compounds may be monomers or oligomers.

Monomers

Monomers herein are defined to be compounds having one polymerizable, ethylenically unsaturated group. Monomers preferably have a molecular weight of less than 300, in particular less than 200, g/mol. They serve in particular as reactive diluents. Possible monomers are, for example selected from C1-C20-alkyl (meth)acrylates, vinyl esters of carboxylic acids comprising up to 20 carbon atoms, vinylaromatics having up to 20 carbon atoms, ethylenically unsaturated nitriles, vinyl ethers of alcohols comprising 1 to 10 carbon atoms.

Vinyl esters of carboxylic acids having 1 to 20 carbon atoms are, for example, vinyl laureate, vinyl stearate, vinyl propionate, vinyl versatate and vinyl acetate.

Suitable vinylaromatic compounds are vinyltoluene, α- and p-methylstyrene, α-butylstyrene, 4-n-butylstyrene, 4-n-decylstyrene and preferably styrene.

Examples of nitriles are acrylonitrile and methacrylonitrile.

Vinyl methyl ether or vinyl isobutyl ether may be mentioned as vinyl ethers. Vinyl ethers of alcohols comprising 1 to 4 carbon atoms are preferred.

Suitable (meth)acrylates are in particular C1- to C10-alkyl acrylates and methacrylates, especially C1- to C8-alkyl acrylates and methacrylates.

Methyl acrylate, ethyl acrylate, n-butyl acrylate, n-hexyl acrylate, octyl acrylate and 2-ethylhexyl acrylate and mixtures of these monomers are very particularly preferred.

In addition polar monomers being substituted by an isocyanate, amino, amido, epoxy, hydroxyl or acid groups are also suitable.

For example, monomers having carboxyl, sulfo or phosphonic acid groups (e.g. vinylphosphonic acid) may be mentioned. Carboxyl groups are preferred. For example, acrylic acid, methacrylic acid, itaconic acid, maleic acid or fumaric acid or acryloyloxypropionic acid may be mentioned.

Further monomers are, for example, also monomers comprising hydroxyl groups, in particular C1-C10-hydroxyalkyl (meth)acrylates, (meth)acrylamide and monomers comprising ureido groups, such as ureido (meth)acrylates.

Mono(meth)acrylates of dihydric or polyhydric alcohols, e.g. monoacrylates or monomethacrylates of ethylene glycol or propylene glycol, may also be mentioned as further monomers.

Reaction products of (meth)acrylic acid and monoepoxides, e.g. phenyl glycidyl ether or glycidyl versatate, are also suitable.

Phenyloxyethylglycol mono(meth)acrylate, glycidyl acrylate, glycidyl methacrylate, amino (meth)acrylates, such as 2-aminoethyl (meth)acrylate, or N-vinylpyrrolidone or N-vinyl-N-methylacetamide may also be mentioned as further monomers.

In a preferred embodiment monomers are compounds with a (meth)acryloyl group.

Oligomers

Oligomers herein are defined to be compounds having two to ten polymerizable, ethylenically unsaturated groups. Compounds having on average from 1.5 to 6, in particular from 2 to 5 polymerizable groups are preferred.

The weight average molecular weight Mw of the oligomers is preferably at least 300, more preferably at least 500 g/mol; preferably Mw is less than 5000, particularly preferably less than 3000, g/mol (determined by gel permeation chromatography using polystyrene as a standard and tetrahydrofuran as an eluent).

The oligomers are in particular (meth)acryloyl compounds.

The oligomers are in particular (meth)acrylates of polyfunctional alcohols or of alkoxylated polyfunctional alcohols.

Examples of such alcohols are bifunctional alcohols, such as ethylene glycol, diethylene glycol, triethylene glycol, propylene glycol, dipropylene glycol, tripropylene glycol, butanediol, pentanediol, hexanediol, neopentyl glycol, alkoxylated phenolic compounds, such as ethoxylated or propoxylated bisphenols, cyclohexanedimethanol, trifunctional and higher-functional alcohols, such as glycerol, trimethylolpropane, butanetriol, trimethylolethane, pentaerythritol, ditrimethylolpropane, dipentaerythritol, sorbitol, mannitol and the corresponding alkoxylated, in particular ethoxylated and propoxylated, alcohols.

The alkoxylated alcohols are obtainable in a known manner by reacting the above alcohols with alkylene oxides, in particular ethylene oxide or propylene oxide. The degree of alkoxylation to the hydroxyl group is preferably from 0 to 10, i.e. 1 mol of hydroxyl group can preferably be alkoxylated with up to 10 mol of alkylene oxides.

(Meth)acrylates of polyesterols may also be mentioned as oligomers.

Suitable polyesterols are, for example, those which can be prepared by esterification of polycarboxylic acids, preferably dicarboxylic acids, with polyols, preferably diols. The starting materials for such polyesters containing hydroxyl groups are known to the person skilled in the art. Preferably used dicarboxylic acids are succinic acid, glutaric acid, adipic acid, sebacic acid, o-phthalic acid, the isomers and hydrogenation products thereof and esterifiable derivatives, such as anhydrides or dialkyl esters of said acids. Maleic acid, fumaric acid, tetrahydrophthalic acid or the anhydrides thereof are also suitable. Suitable polyols are the above mentioned alcohols, preferably ethylene glycol, 1,2- and 1,3-propylene glycol, butane-1,4-diol, hexane-1,6-diol, neopentyl glycol, cyclohexanedimethanol and polyglycols of the ethylene glycol and propylene glycol type.

(Meth)acrylates of polyesterols can be prepared in a plurality of stages or in one stage, as described, for example, in EP 279 303, from acrylic acid, polycarboxylic acid and polyol.

Epoxide (meth)acrylates or urethane (meth)acrylates may also be suitable oligomers.

Epoxide (meth)acrylates are, for example, those which are obtainable by reacting epoxidized olefins or poly- or mono- or diglycidyl ethers, such as bisphenol A diglycidyl ether, with (meth)acrylic acid.

The reaction is known to the person skilled in the art and is described, for example, in R. Hofmann, U.V. and E.B. Curing Formulation for Printing Inks and Paints, London 1984.

Urethane (meth)acrylates are in particular reaction products of hydroxyalkyl (meth)acrylates with poly- or diisocyanates (cf. also R. Hofmann, U.V. and E.B. Curing Formulation for Printing Inks and Paints, London 1984).

The above compounds may comprise further functional groups, for example hydroxyl groups which are not esterified with (meth)acrylic acid.

Further oligomers are, for example, low molecular weight unsaturated polyesters which in particular have double bonds as a result of a content of maleic acid or fumaric acid and are copolymerizable.

Preferred oligomers are fluid at 20° C., 1 bar.

In a preferred embodiment, oligomers are (meth)acryloyl compounds, in particular (meth)acrylates of polyfunctional alcohols, in particular meth)acryloyl compounds which, apart from hydroxyl groups or ether groups have no further functional groups.

Most preferred oligomers are (meth)acryloyl compounds which are fluid at 20° C., 1 bar, and have from 2 to 4 (meth)acryloyl groups.

Polymers

In addition to the above monomers and/or oligomers the radiation curable composition may comprise polymers which already have a high molecular weight. Such polymers may have a molecular weight Mw of more than 3000, in particular more than 5000 (determined by gel permeation chromatography using polystyrene as a standard and tetrahydrofuran as an eluent).

Suitable polymers may have reactive groups, for example polymerizable, ethylenically unsaturated groups or other functional groups which react with corresponding groups of any monomer or oligomer, so that bonding to the above monomers or oligomers takes place during the curing. Also suitable, however, are polymers without such groups, which subsequently form an independent continuous phase or an interpenetrating network in the coating obtained.

Suitable polymers are, for example, polyesters, polyadducts, in particular polyurethanes, or polymers obtainable by free radical polymerization. Polymers obtainable by free radical polymerization are particularly suitable, preferably those which comprise at least 40% by weight, particularly preferably at least 60% by weight, very particularly preferably at least 80% by weight, of so-called main monomers, selected from C1-C20-alkyl (meth)acrylates, vinyl esters of carboxylic acids comprising up to 20 carbon atoms, vinylethers of monoalcohols comprising up to 20 C atoms vinylaromatics having up to 20 carbon atoms and/or ethylenically unsaturated nitriles.

In a preferred embodiment the radiation curable composition which is used as ink-jet printing ink comprises (meth) acryloyl compounds.

In particularly preferred embodiment the radiation curable composition which is used as ink-jet printing ink comprises monomers with (meth)acryloyl groups (for short (meth)acryloyl monomers and/or oligomers with (meth) acryloyl compounds (for short (meth)acryloyl oligomers.

In a specifically preferred embodiment the radiation curable composition which is used as ink-jet printing ink comprises (meth)acryloyl oligomers, preferably (meth)acryloyl oligomers with two to five (meth)acryloyl groups.

In a preferred embodiment at least 70% by weight of all radiation curable compounds of the radiation curable composition are (meth)acryloyl compounds and the N-vinyloxazolidinone.

Besides the radiation curable compounds, the radiation curable composition may comprise additives, for example pigments, including effect pigments, dyes, fillers, stabilizers, e.g. UV absorbers, antioxidants or biocides, leveling agents, antifoams, wetting agents, antistatic agents, etc.

The radiation curable composition may comprise water or organic solvents. Preferably it comprises little or no water or organic solvent (unreactive compound fluid at 20° C., 1 bar).

In a preferred embodiment, the radiation curable composition comprises less than 20% by weight of water or organic solvents, particularly preferably less than 10 parts by weight and in particular less than 5 parts by weight of water or organic solvents, based on 100 parts by weight of printing ink. Very particularly preferably, the radiation curable composition comprises substantially no or less than 1 by weight of % water or organic solvents.

Preferably, the radiation curable composition comprises at least one photoinitiator.

The photoinitiator may be, for example, so-called α-cleavers, i.e. photoinitiators in which a chemical bond is cleaved so that 2 free radicals form, which initiate the further crosslinking or polymerization reactions.

For example, acylphosphine oxides (Lucirin® brands from BASF), hydroxyalkylphenones (e.g. Irgacure® 184), benzoin derivatives, benzil derivatives, dialkyloxyacetophenones may be mentioned.

In particular, they may also be so-called H-abstractors which remove a hydrogen atom from the polymer chain; for example, these are photoinitiators having a carbonyl group. This carbonyl group shifts into a C—H bond with formation of a C—C—O—H group.

In particular, acetophenone, benzophenone and derivatives thereof may be mentioned here.

Benzoins or benzoin ethers may also be mentioned.

Photoinitiators can be used alone or as a mixture, mixtures of photoinitiators having different modes of action may also be particularly suitable.

Photoinitiators can also be bound to an above polymer or oligomer, if present.

In the case of thermal curing or a combination of radiation curing and thermal curing, one or more thermally activatable initiators, such as peroxides, azo compounds, etc., may be added.

The radiation curable composition generally comprises at least one dye or one pigment.

The radiation curable composition can be prepared in any desired manner by adding the individual constituents in any sequence and mixing.

The radiation curable composition is used as printing ink in ink-jet printing.

The radiation curable composition is printed on substrates and preferably subsequently cured by radiation.

Different substrates may be printed, for example paper, metal films or polymer films, like polyethylene terephthalate, polyamide, polystyrene, polyvinylchloride, polycarbonate, polyolefines like polyethylene or polypropylene or aluminium In particular polyolefine substrates like polyethylene substrates or polypropylene substrates may be printed, even if they are not corona pretreated.

A preferred embodiment of this invention is an ink-jet printing process, wherein a polypropylene substrate or a polyethylene substrate are printed. A most preferred substrate is polyethylene.

The radiation curable composition has good performance characteristics in ink-jet printing; it has a high reactivity in radiation curing, a low viscosity and results in a print with very good adhesion, especially good adhesion to polymer films, in particular to polypropylene. In particular it is an advantage of the radiation curable composition that less reactive diluent is required. Compared to other reactive diluents less N-vinyl oxazolidinone is required to obtain a radiation curable composition of a sufficient low viscosity and very good suitability as printing ink for ink jet.

EXAMPLES

Example 1

As N-vinyloxazolidinone a compound of formula I with $R_1$ to $R_4$ being a hydrogen atom was used (for short NVO) and a compound with $R_1$ being a methyl radical and all of $R_2$ to $R_4$ being hydrogen (N-vinyl-5-methyl oxazolidinone, for short NVMO) was used.

NVO was used as reactive diluent in ink-jet printing inks.

For comparison identical ink-jet printing inks have been prepared using N-vinylcaprolactam (NVC) and 4-acryloyl morpholine (ACMO) which are well known reactive diluents.

For this purpose, a printing ink was prepared by mixing oligomers containing acrylate groups (Laromer® products of BASF), dispersants and pigment (pigment paste) and then adding the above monomers and as further monomer isobornyl acrylate.

The printing inks were applied to the substrate by means of a bar applicator and exposed to an energy of 120 W/m on a UV exposure unit equipped with a high pressure UV mercury lamp. The coated substrate was lying on belt which is passed under the UV lamp. With low speeds of the belt the exposure to radiation is long. The speed of the belt was increased in steps of 5 m/min and checked whether the coating was cured by mechanical testing (scratching). The highest belt speed possible is a measure of reactivity.

Adhesion

For the investigation of the adhesion of the obtained coatings, a "Crystal" Scotch adhesive tape was used. The adhesive tape was stuck to the exposed coating and peeled off again and it was determined whether the coating had become detached therewith. The belt speed for the preparation of the layers was 15 m/min, respectively 3 times 15 m/min (3×15). The layer thickness was 6, respectively 12 μm.

Rating 0 (No Delamination)-5 (Complete Delamination)

The composition of the printing inks and results of the adhesion test are to be found in Table 1.

TABLE 1

| Inkjet printing ink | | | | |
|---|---|---|---|---|
| Example | Example 1 | Example 2 | Comparison Example 1 | Comparison Example 2 |
| Monomer | NVO | NVMO | ACMO | NVC |
| Parts by weight of the above monomer | 30 | 30 | 30 | 30 |
| Isobornyl acrylate [parts by weight] | 32 | 32 | 32 | 32 |
| Laromer ® PO 77 F | 8 | 8 | 8 | 8 |
| Laromer ® DPGDA | 10.4 | 10.4 | 10.4 | 10.4 |
| Mill Base UV Cyan (pigment) [parts by weight] | 10 | 10 | 10 | 10 |
| Lucirin ® TPO XL [parts by weight] (photoinitiator) | 3.5 | 3.5 | 3.5 | 3.5 |
| Darocur ® 1173 [parts by weight] (photoinitiator) | 4 | 4 | 4 | 4 |
| Further additives (parts by weight) | 2.1 | 2.1 | 2.1 | 2.1 |
| Total [parts by weight] | 100 | 100 | 100 | 100 |
| Viscosity I.C.I at 23° C., 1/20 s [mPas] | Lower 10 | Lower 10 | 13 | 15 |
| Belt speed [m/min] at which sample can still be cured (layer 6 μm) (measure of the reactivity) | 40 | 40 | 35 | 30 |
| Adhesion (layer 6 μm, belt speed 15 m/min) | | | | |
| Polyethylene terephthalate film (PET X13 Melinax) | 0 | 1 | 5 | 0 |
| Polyethylene film | 0 | 1 | 2 | 1 |
| Polypropylene film | 1 | 1 | 3 | 1 |
| Adhesion (layer 12 μm, belt speed 3 × 15 m/min) | | | | |
| Polyethylene terephthalate film | 5 | 0 | 5 | 5 |
| Polyethylene film | 0 | 0 | 5 | 5 |
| Polypropylene film | 5 | 5 | 5 | 5 |
| Adhesion (layer 24 μm, belt speed 3 × 15 m/min for comparison examples, 2 × 15 m/min for examples) | | | | |
| Polyethylene terephthalate film | 5 | 5 | 5 | 5 |
| Polyethylene film | 0 | 0 | 5 | 5 |
| Polypropylene film | 0 | 0 | 5 | 5 |

The invention claimed is:

1. A process, comprising applying a printing ink to a substrate and exposing the printing ink to an energy to form a coated substrate, wherein the printing ink comprises a radiation curable composition comprising an N-vinyloxazolidinone of formula (I):

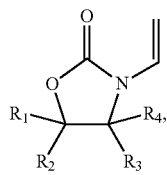

in which $R_1$ to $R_4$ independently from each other are a hydrogen atom or an organic radical having not more than 10 carbon atoms.

2. The process of claim 1, wherein at least two of $R_1$ to $R_4$ are a hydrogen atom and any remaining $R_1$ to $R_4$ are an organic radical having not more than 10 carbon atoms.

3. The process of claim 1, wherein:
all of $R_1$ to $R_4$ are hydrogens,
$R_1$ is a C1 to C4 alkyl group, and $R_2$ to $R_4$ are hydrogens, or
$R_1$ and $R_2$ are hydrogens, and $R_3$ and $R_4$ are independently a C1 to C4 alkyl group.

4. The process of claim 1, wherein the radiation curable composition comprises the N-vinyloxazolidinone in an amount of from 0.5 to 80% by weight.

5. The process of claim 1, wherein the radiation curable composition further comprises a (meth)acryloyl compound comprising at least one (meth)acryloyl group.

6. The process of claim 5, wherein the radiation curable composition comprises at least one (meth)acryloyl compound having two to five (meth)acryloyl groups.

7. The process of claim 5, wherein at least 70% by weight of all radiation curable compounds of the radiation curable composition are (meth)acryloyl compounds and the N-vinyloxazolidinone.

8. The process of claim 1, wherein the radiation curable composition comprises less than 10% by weight of ater or organic solvents.

9. The process of claim 1, wherein the radiation curable composition comprises at least one photoinitiator.

10. The process of claim 1, wherein the process is an ink jet printing process.

11. The process of claim 10, wherein the radiation curable composition is printed on a substrate and subsequently cured by radiation.

12. The process of claim 10, wherein the substrate is a polypropylene substrate.

* * * * *